United States Patent [19]

Armand

[11] Patent Number: 5,256,821
[45] Date of Patent: Oct. 26, 1993

[54] METHOD OF SYNTHESIS OF SULPHONYLIMIDES

[75] Inventor: Michel B. Armand, Saint Martin d Uriage, France

[73] Assignees: Societe Nationale Elf Aquitaine, Courbevoie, France; Hydro-Quebec, Quebec, Canada

[21] Appl. No.: 587

[22] Filed: Jan. 5, 1993

Related U.S. Application Data

[63] Continuation of Ser. No. 830,749, Feb. 7, 1992, abandoned, which is a continuation of Ser. No. 460,138, filed as PCT/FR89/00512 on Oct. 4, 1989, abandoned.

[30] Foreign Application Priority Data

Oct. 5, 1988 [FR]  France ................. 88/13005

[51] Int. Cl.$^5$ ........................... C07C 303/38
[52] U.S. Cl. ............................... 564/82
[58] Field of Search .......................... 564/82

[56] References Cited

FOREIGN PATENT DOCUMENTS 2002065 7/1971 Fed. Rep. of Germany.
2002066 7/1971 Fed. Rep. of Germany.
2239817 2/1974 Fed. Rep. of Germany.

Primary Examiner—Allen J. Robinson
Assistant Examiner—Scott C. Rand
Attorney, Agent, or Firm—Oblon, Spivak, McClelland, Maier & Neustadt

[57] ABSTRACT

Method for the synthesis of sulfonylimidides having the formula $M((RSO_2)_2N)_y$, wherein M is a metal or an ammonium radical quaternary or not, the Rs, which may be identical or similar are organic monovalent radicals, particularly hydrocarbyles and preferably perfluorohydrocarbyles, in $C_1$ to $C_{12}$, and y is the valence of M. On the one hand, silazane component selected amongst the silazane compounds $M(((R_2)_3Si)_2N)_y$ or the associations of a silazane derivative $A((R_2)_3Si)_2N$ or a fluoride $M_1F_z$ of low cross-linking energy is reacted with, on the other hand, at least one sulfonic halogenite component consisting of a sulfonyl fluoride $RSO_2F$ or in the association of a sulfonyl chloride $RSO_2Cl$ with a fluoride $M_1F_z$, M, R and y having the above-mentioned significations, M being selected amongst the Ms and being optionally identical to M, z being the valence of $M_1$ and $R_2$ representing an alkyl in $C_1$ to $C_4$. The imidides obtained for which the $R_2$ are perfluorated radicals and M is an alkaline metal such as Li are usable in association with polyethers for the production of materials of the ionic conduction type for all solid generators in thin films.

22 Claims, No Drawings

METHOD OF SYNTHESIS OF SULPHONYLIMIDES

This application is a continuation of application Ser. No. 07/830,749 filed on Feb. 7, 1992, now abandoned, which is a continuation of application Ser. No. 07/460,138, filed as PCT/FR89/00512 on Oct. 4, 1989, now abandoned.

The invention relates to a method of synthesis of sulthonylimides and more particularly of perfluorosulphonylimides, symmetric or otherwise.

The perfluorosulphonylimides corresponding to the general formula $M((R_FSO_2)_2N)_y$, in which M denotes a metal or an ammonium group, quaternary or otherwise, the $R_F$ groups, which are identical in the case of symmetric amides and different in the case of unsymmetric amides, denote monovalent perfluorohydrocarbyl radicals and especially perfluoroalkyl radicals such as $CF_3$, $C_2F_5$, $C_4F_9$ or perfluoroaryl radicals such as $CF_5$, and y is a number equal to the valency of M, are of interest owing to the properties linked with the corresponding anion. In effect, the delocalization of the anion charge over a number of electronegative centres, namely F, O and N atoms, induces a basicity and a nucleophilic character which are weak. The stability of the covalent bonds additionally permits an extended range of redox stability, in particular to anode potentials. Alkali metal, and especially lithium, perfluorosulphonylimides can be employed in particular for forming solid solutions with macromolecular materials of the polyether type, solid solutions which find an application as polymeric solid electrolytes in the production of all-solid primary or secondary generators in the form of thin films (U.S. Pat. No. 4,505,997).

The amides defined by the abovementioned formula can be obtained,, for example, from the corresponding anhydrides $(R_FSO_2)_2O$ by making use of any of the methods of synthesis outlined in reference U.S. Pat. No. 4,505,997.

The first of these methods consists firstly in reacting the anhydride $(RSO_2)_2O$ with urea and a sulphonic acid $R_FSO_3H$ according to the reaction:

$(R_FSO_2)_2O + R_FSO_3H + OC(NH_2)_2 \rightarrow (R_FSO_2)_2NH + NH_4CF_3SO_3 + CO_2 \uparrow$ The products obtained after reaction are then dissolved in water and the addition of tetrabutylammonium bromide to the solution obtained makes it possible to precipitate the tetrabutylamonium imide of formula $(Bu)_4NN(R_FSO_2)_2$. The sodium imide $NaN(R_FSO_2)_2$ is formed by an ionic exchange reaction between this compound and sodium tetraphenylborohydride. Salts of other metals can be prepared by the action of hydroxides, oxides or carbonates of the chosen metals on sodium imide.

The second of the said methods consists in reacting the anhydride $(R_FSO_2)_2O$ with pyridine and ammonium chloride according to the reaction scheme:

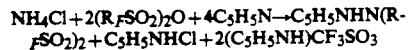

The products of the reaction are dissolved in water and the addition of tetrabutylammonium bromide to the solution obtained results in the precipitation of tetrabutylammonium imide. This is then continued to sodium imide and then to the salts of other metals as indicated in the case of the first method.

The abovementioned methods are not satisfactory for a large scale production of amides because the overall yields are low and the precursor anhydrides $(R_FSO_2)_2O$ are not easily accessible.

It is also possible to obtain the abovementioned amides from the precursors $R_FSO_2F$ by making use of the four-stage method of synthesis proposed by J. Foropoulos and D. D. Desmarteau in the journal Inorganic Chemistry, vol. 23 (1984), No. 23, pages 3720 to 3723.

In this method, which leads to sodium imide, the reaction scheme is the following:

1) 

2) $H_2NSO_2R_F + NaOCH_3 \longrightarrow NaNHSO_2R_F + HOCH_3$

3) $2NaNHSO_2R_F + ((CH_3)_3Si)_2NH \longrightarrow$

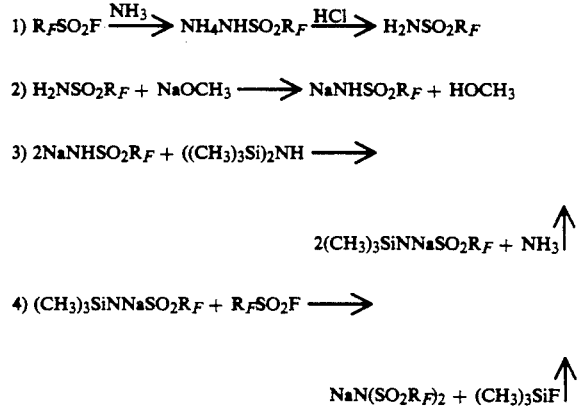

Apart from a low yield, generally lower than 50%, this method cannot be generalized to the use of precursors of the sulphonyl chloride type $R_FSO_2Cl$, because, when reacted with ammoniac these compounds do not give the amide $H_2NSO_2R_F$ which is produced in the first stage of the method and which is necessary for making use of the subsequent stages of this method.

Reference DE-A-2,239,817 proposes a method of synthesis of alkali metal perfluoroalkanesulphonylimides by reaction of a perfluoroalkanesulphonyl fluoride with an alkali metal derivative of an N-trimethylsilylperfluoroalkanesulphonamide, it being possible to obtain the said sulphonamide derivative either by reaction of a perfluoroalkanesulphonyl fluoride with an alkali metal derivative of hexamethyldisilazane or by reaction of an alkali metal derivative of a perfluoroalkanesulphonamide with hexamethyldisilazane.

Reference DE-A-2,002,065 describes particularly (cf. Example 18) the preparation of bismethanesulphonylimide by first of all preparing N-trimethylsilylmethanesulphonamide by reaction between hexamethyldisilazane and methanesulphonyl chloride, and by then reacting the said sulphonamide with methanesulphonyl chloride.

A method of synthesis of sulphonylimides of formula $M((RSO_2)_2N)_y$, in which each of the symbols R, which are identical or different, denotes a hydrocarbyl radical and more particularly a perfluorohydrocarbyl radical $R_F$, and M and Y have the meanings given above is now proposed, from precursors of the corresponding sulphonyl fluoride or chloride type, which produces high yields, is extremely flexible to use on any scale and, furthermore, relies on reactants which are commonly employed and are available from commercial sources.

The method according to the invention for the synthesis of sulphonylimides of formula $M((RSO_2)_2N)_y$, in which M denotes a metal or an ammonium radical $N(R_1)_4$, the symbols $R_1$, which are identical or different, denoting a hydrogen atom or a $C_1$-$C_8$ hydrocarbyl radical, each of the symbols R, which are identical or different, denotes a monovalent $C_1$-$C_{12}$ organic radical and y is a number equal to the valency of M, is of the type in which, on the one hand, a silazane component containing a silazane compound of formula $M(((R_2)_3Si)_2N)_y$, in which M and y have the abovementioned meanings and $R_2$ is a $C_1$-$C_4$ alkyl or a silazane derivative of formula $A((R_2)_3Si)_2N$, in which A denotes a hydrogen atom or an $(R_2)_3Si$ radical where $R_2$ has the above meaning, is reacted with, on the other hand, at least one sulphonyl halide component containing a sulphonyl fluoride $RSO_2F$ or a sulphonyl chloride $RSO_2Cl$, R having the abovementioned meaning, and it is characterized in that it consists in bringing the silazane component consisting of a silazane compound $M[((R_2)_3Si)_2N]_y$ into contact with a sulphonyl halide component consisting of a sulphonyl fluoride $RSO_2F$ in a molar ratio of the compound $RSO_2F$ to the silazane compound substantially equal to 2y:1 to form a symmetric imide in a single stage or in that it employs a silazane component resulting from the association of a silazane derivative $A[(R_2)_3Si]_2N$ and of a fluoride $M_1F_z$ and/or at least one sulphonyl halide component resulting from the association of a sulphonyl chloride $RSO_2CL$ and of a fluoride $M_1F_z$, the said fluoride $M_1F_z$ being a fluoride of low lattice energy for which $M_1$ is chosen from the same group as M and may be identical with M and z is the valency of $M_1$.

According to one embodiment, the imide is produced by reacting a silazane component which results from the association of a silazane derivative $A((R_2)_3Si)_2N$ and of a fluoride $M_1F_z$, with a single sulphonyl halide component consisting of a sulphonyl fluoride $RSO_2F$ or with a first and then a second sulphonyl halide component, one of which consists of a sulphonyl fluoride $RSO_2F$ and the other of a sulphonyl fluoride $R'SO_2F$, R' belonging to the same group as R but being different from the latter, the molar ratio of the silazane derivative to the fluoride $M_1F_z$ being preferably at most substantially equal to z:1 when the symbol A denotes an $(R_2)_3Si$ radical or to 2 z:1 when the symbol A denotes a hydrogen atom.

According to another embodiment, the imide is formed by reacting a silazane component which consists of a silazane compound $M(((R_2)_3Si)_2N)_y$, with a single sulphonyl halide component resulting from the association of a sulphonyl chloride $RSO_2Cl$ and of a fluoride $M_1F_z$, or with a first and then a second sulphonyl halide component, one of which results from the association of a sulphonyl chloride $RSO_2Cl$ and of a fluoride $M_1F_z$ while the other consists of a sulphonyl fluoride $R'SO_2F$ or results from the association of a sulphonyl chloride $R'SO_2Cl$ and of the fluoride $M_1F_z$, R' belonging to the same group as R but being different from the latter, the molar ratio of the compound $RSO_2Cl$ or $R'SO_2Cl$ to the fluoride $M_1F_z$ being preferably at most substantially equal to z:1.

According to yet another embodiment, the imide is produced by reacting a silazane component resulting from the association of a silazane derivative $A((R_2)_3Si)_2N$ and of a fluoride $M_1F_z$, with a single sulphonyl halide component resulting from the association of a sulphonyl chloride $RSO_2Cl$ and of the fluoride MF. or with a first and then a second sulphonyl halide component, one of which results from the association of a sulphonyl chloride $RSO_2Cl$ with the fluoride $M_1F_z$ and the other consists of a sulphonyl fluoride $R'SO_2F$ or results from the association of a sulphonyl chloride $R'SO_2Cl$ and of the fluoride $M_1F_z$, R' belonging to the same group as R but being different from the latter, the molar quantity c of the fluoride $M_1F_z$ to be associated with the molar quantities a of the silazane derivative and b of the sulphonyl chloride or chlorides being preferably such that c is at least substantially equal to $(1/z) \times (a+b)$ when the symbol A of the silazane derivative is a $(R_2)_3Si$ radical or to $(1/z) \times [(a/2) + b]$ when the symbol A of the silazane derivative is a hydrogen atom.

The silazane compounds $M(((R_2)_3Si)_2N)_y$ which are employed in the preparation of the imide are preferably those in the case in which M denotes a metal of groups I and II of the Periodic Classification of the Elements, especially Li, Na, K, Ag and Mg, or an —$NH_4$ or —$N(R_3)_4$ group, $R_3$ denoting a $C_1$-$C_6$ alkyl radical or a phenyl radical.

The sulphonyl halides, namely sulphonyl fluorides and chlorides, are advantageously chosen from those in the case of which each of R and R' denotes a $C_1$-$C_2$-hydrocarbyl radical, the said radical being more particularly a perfluorohydrocarbyl radical $R_F$ such as a perfluoroalkyl, perfluorocycloalkyl or perfluoroaryl radical. The radical $R_F$ is preferably a $C_1$-$C_6$ perfluoroalkyl radical such as $CF_3$, $C_2F_5$, $C_3F_7$, $C_4F_9$, $C_5F_{11}$, $C_5F_3$ or a perfluorophenyl radical $C_6F_5$.

The radical $R_2$ of the silazane compound $M(((R_2)_3Si)_2N)_y$ or of the silazane derivative $A((R_2)_3Si)_2N$ is preferably a methyl or ethyl radical and very particularly a methyl radical.

The fluoride $M_1F_z$ of low lattice energy, which is employed in the method of synthesis is, for example, chosen from the fluorides KF, AgF and $N(R_4)_4F$, the symbols $R_4$, which are identical or different, denoting a hydrogen atom, a $C_1$-$C_6$ alkyl radical or a phenyl radical.

According to one form of implementation of the method according to the invention, which leads to the production of a symmetric imide, a single sulphonyl halide component is reacted with the silazane component in such quantities as to make the molar ratio of the sulphonyl fluoride or chloride of the sulphonyl halide component to the silazane compound or derivative of the silazane component preferably substantially equal to:

2y:1 when the silazane component contains a compound of formula $M(((R_2)_3Si)_2N)_y$, 2:1 when the silazane component contains a derivative of formula $A((R_2)_3Si)_2N$ in the case of which A is an $(R_2)_3Si$ radical, and 3:2 when the silazane component contains a derivative of formula $A((R_2)_3Si)_2N$ in the case of which A is a hydrogen atom.

According to another form of implementation of the method according to the invention, which results in the production of an unsymmetric imide, in a first stage a first sulphonyl halide component is reacted with the silazane component in such quantities as to make the molar ratio of the sulphonyl fluoride or chloride of the sulphonyl halide component to the silazane compound or derivative preferably substantially equal to y:1 when the silazane component contains a compound of formula $M(((R_2)_3Si)_2N)_y$, and 1:1 when the silazane component contains a derivative of formula $A((R_2)_3Si)_2N$, and then, in a second stage, the reaction mixture originating from the first stage is brought into contact with a second sulphonyl halide component, different from the first and employed in a molar quantity substantially equal to that of the first sulphonyl halide component when the starting silazane component contains a compound $M(((R_2)_3Si)_2N)_y$ or a derivative $A((R_2)_3Si)_2N$ in the case of which A is an $(R_2)_3Si$ radical or substantially equal to half the quantity of the first sulphonyl halide component when the starting silazane component contains a derivative $A((R_2)_3Si)_2N$ in the case of which A is a hydrogen atom.

According to a particular form of implementation, which results in the production of an unsymmetric imide, the sulphonyl chloride $RSO_2Cl$ of a first sulphonyl halide component associating the said sulphonyl chloride and a fluoride $M_1F_z$ is first of all reacted with a silazane component consisting of a compound $Ml(((R_2)_3Si)_2N)_z$, in such quantities as to make the molar ratio of the sulphonyl chloride to the silazane compound substantially equal to $z:1$, $z$ being the valency of $M_1$, and the resulting reaction mixture is then brought into contact with a second sulphonyl halide component consisting of a sulphonyl fluoride $R'SO_2F$, $R'$ denoting a radical chosen from the same group as R but different from the latter, and with the fluoride $M_1F_z$ of the first sulphonyl halide component, using quantities of the compounds $R'SO_2F$ and $M_1F_z$ such as to make the molar ratio $R'SO_2F:RSO_2Cl$ substantially equal to 1:1 and so as to make the molar ratio $RSO_2Cl:M_1F_z$ substantially at most equal to $z:1$, the unsymmetric imide formed corresponding to the formula $M_1(RSO_2NSO_2R')_z$.

According to another particular form of implementation, which also results in the production of an unsymmetric imide, a first sulphonyl halide component consisting of a sulphonyl fluoride $RSO_2F$ is first of all reacted with the silazane derivative $A((R_2)_3Si)_2N$ which forms a silazane component with a fluoride $M_1F_z$, in such quantities as to make the molar ratio $RSO_2F$:silazane derivative substantially equal to 1:1, and then to the resulting reaction mixture there is added, on the one hand, a sulphonyl chloride $R'SO_2Cl$, which may also form a sulphonyl halide component with the fluoride $M_1F_z$, R' denoting a radical chosen f rom the same group as R but different from the latter and, on the other hand, the said fluoride $M_1F_z$, using quantities of sulphonyl chloride $R'SO_2Cl$ and of fluoride $M_1F_z$ such as to make the molar ratio $R'SO_2Cl$:silazane derivative substantially equal to 1:1 and the ratio $R'SO_2Cl:M_1F_z$ at most substantially equal to $z:2$, when the silazane derivative has the formula $((R_2)_3Si)_3N$, and so as to make the molar ratio $R'SO_2Cl$:silazane derivative substantially equal to 1:2 and the molar ratio $R'SO_2Cl:M_1F_z$ at most substantially equal to $z:2$, when the silazane derivative has the formula $((R_2)_3Si)_2NH$, the imide produced having the formula: $M_1(RSO_2NSO_2R')_z$.

The contact between the ingredients which react according to the invention to form the amides is advantageously brought about in a solvent medium consisting of a polar aprotic solvent or of a mixture of such solvents. Polar aprotic solvents which are particularly suitable are ethers such as tetrahydrofuran, diglyme and dimethoxyethane, amides such as dimethylformamide and dimethylethyleneurea, and nitriles such as acetonitrile.

The following examples are given to illustrate the invention, no limitation being implied.

EXAMPLE 1

6.04 g of perfluorobutanesulphonyl fluoride were added to 3.66 g of sodium bis(trimethylsilyl)amide in solution in 20 ml of anhydrous tetrahydrofuran (THF). The mixture thus obtained was stirred at room temperature for 48 hours.

The reaction took place according to the following reaction scheme:

$$2C_4F_9SO_2F + Na((CH_3)_3Si)_2N \rightarrow Na(C_4F_9SO_2)_2N + 2(CH_3)_3SiF \uparrow$$

The imide produced by the reaction, namely $Na(C_4F_9SO_2)_2N$, was isolated by evaporation of the solvent.

The acid corresponding to this imide, namely $H(C_4F_9SO_2)_2N$, can be extracted with ethyl ether from the aqueous solution of the salt, acidified with a strong acid such as $H_2SO_4$. The amides of other metals can then be prepared by the action of the hydroxides, oxides or carbonates of the appropriate metals on the above-mentioned acid.

EXAMPLE 2

15.2 g of trifluoromethanesulphonyl fluoride were injected over a period of 3 hours into 50 ml of a 1M solution of the potassium derivative of hexamethyldisilazane in dimethoxyethane (DME), maintained at $-20°$ C. The reaction mixture thus formed was brought back to room temperature and kept stirred at this temperature for a period of 12 hours.

The imide formed during the reaction, namely potassium bis(trifluoromethanesulphonyl)imide of formula $K(CF_3SO_2)_2N$, was isolated in an 83% yield after evaporation of the solvent.

The reaction took place according to the following reaction scheme:

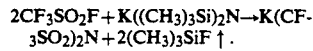

$$2CF_3SO_2F + K((CH_3)_3Si)_2N \rightarrow K(CF_3SO_2)_2N + 2(CH_3)_3SiF \uparrow .$$

The potassium salt of hexamethyldisilazane was prepared by reaction of hexamethyldisilazane with potassium hydride.

The acid $H(CF_3SO_2)_2N$ can be obtained in the pure state by treatment of the imide $K(CF_3SO_2)_2N$ with anhydrous sulphuric acid and distillation under reduced pressure (0.3 Pa at 90° C.), the said acid being a hygroscopic solid melting at 30°-35° C. The various metal imides derived from said acid can be obtained by reaction of this acid with the hydroxides, oxides or carbonates of the appropriate metals.

EXAMPLE 3

30.2 g of perfluorobutanesulphonyl fluoride in solution in 20 ml of DME were added to 50 ml of a 1M solution of the potassium derivative of hexamethyldisilazane in DME, maintained at $-20°$ C., the said addition being performed over a period of 3 hours. The reaction mixture obtained was then brought back to room temperature and stirred at this temperature for 12 hours.

The imide formed during the reaction, namely potassium bis(perfluorobutanesulphonyl)imide of formula $K(C_4F_9SO_2)_2N$, was isolated by distillation of the DME solvent, and was then purified by recrystallization from water.

The reaction took place according to the following reaction scheme:

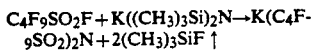

EXAMPLE 4

30.4 g of trifluoromethanesulphonyl fluoride were injected slowly into 100 ml of a 1M solution of the lithium derivative of hexamethyldisilazane in THP, maintained at −18° C. After the reaction mixture thus obtained returned to room temperature, the solvent was evaporated off from the said mixture to leave a solid residue of lithium bis(trifluoromethanesulphonyl)imide. After purification by washing with dichloromethane, 26 g of the said lithium compound were obtained.

The reaction took place according to the following reaction scheme:

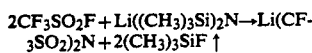

EXAMPLE 5

2.9 g of the compound $Li(CF_3SO_2)_2N$, obtained as described in Example 4, were dissolved with 4.4 g of an ethylene oxide polymer which had a molecular mass equal to $5 \times 10^5$ in 200 ml of acetonitrile. A fraction of 15 ml of the viscous solution obtained was cast on a polytetrafluoroethylene plaque in a glass ring 50 mm in diameter.

After evaporation of the solvent in an oven at 60° C., an elastic and amorphous film, 220 μm in thickness, of the $Li(CF_3SO_2)_2N$/polymer complex was obtained. This material has an ion conductivity of $2 \times 10^5$ ohm$^{-1}$ cm$^{-1}$ at 25° C. and can be employed for forming the solid electrolyte layer and also for producing the binder of the composite positive electrode of primary or secondary all-solid thin-film generators whose negative electrode consists of metallic lithium or of a lithium-based alloy such as a rithium-aluminium alloy.

EXAMPLE 6

1.16 g of anhydrous potassium fluoride KF were added to 5.41 ml of nonamethyltrisilazane in 15 ml of DME. The mixture thus formed was cooled to −20° C. 6.08 g of trifluoromethanesulphonyl fluoride were then added to the cooled mixture. After returning the reaction mixture to room temperature and distilling off the solvent, 3 g of potassium bis(trifluoromethanesulphonyl)imide were obtained.

The reaction took-place according to the following reaction scheme:

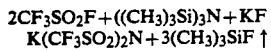

EXAMPLE 7

3.38 ml of nonamethyltrisilazane were added to 25 ml of a 0.5M solution of tetrabutylammonium fluoride in THF, followed by 5.05 g of pentafluoroethanesulphonyl fluoride. The reaction mixture was stirred at room temperature for about 1.5 hours and the solvent was then evaporated off. After evaporation of the solvent 7 g of tetrabutylammonium bis(pentafluoroethanesulphonyl)imide of formula $(C_4H_9)_4N(C_2F_5SO_2)_2N$ were then obtained.

The reaction took place according to the following reaction scheme:

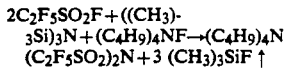

EXAMPLE 8

1.74 g of anhydrous KF were added to 10 ml of a 1M solution of the lithium derivative of hexamethyldisilazane in DME, followed by 2.2 ml of trifluoromethanesulphonyl chloride. The reaction mixture was then stirred at room temperature for 2 hours.

The reaction took place according to the following reaction scheme: $2CF_3SO_2Cl + 3KF + Li((CH_3)_3Si)_2N \rightarrow K(CF_3SO_2)_2N + 2KCl + LiF + 2(CH_3)_3SiF \uparrow$ At the end of the reaction, the KCl and LiF salts were separated from the reaction mixture by filtration and the solution obtained was then subjected to evaporation to remove the solvent and to isolate the imide as evaporation residue.

At the end of the evaporation 3.1 g of imide of formula $K(CF_3SO_2)_2N$ were obtained.

EXAMPLE 9

4.25 ml of hexamethyldisilazane and 1.48 g of $NH_4F$ were added to a solution of 9.55 g of perfluorobutanesulphonyl sulphonyl chloride in 30 ml of DME. The reaction mixture thus formed was stirred at room temperature for 6 hours.

The reaction took place according to the following reaction scheme:

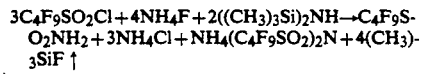

The ammonium chloride was in the form of a precipitate, which was separated off from the reaction mixture by filtration.

The residual solution was subjected to an evaporation to remove the solvent and to form an evaporation residue consisting of a mixture of the imide $NH_4(C_4F_9SO_2)_2N$ and the amide $C_4F_9SO_2NH_2$. Taking up the dry evaporation residue with dichloromethane, followed by filtration, allows the imide, which is insoluble in this solvent, to be isolated.

EXAMPLE 10

17.5 g of anhydrous KF were added to a solution of 22 ml of trifluoromethanesulphonyl chloride in 200 ml of DME, followed by 18.9 ml of nonamethyltrisilazane. The mixture was stirred at room temperature for 72 hours.

The reaction took place according to the following reaction scheme:

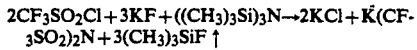

At the end of the reaction period the reaction mixture was filtered to separate off KCl, insoluble in the said mixture. 31 g of the potassium salt of bis(trifluoromethanesulphonyl)imide were obtained by evaporation of the filtrate.

EXAMPLE 11

5.4 ml of nonamethyltrisilazane were added to a solution of 4.4 ml of trifluoromethanesulphonyl chloride in 25 ml of acetonitrile, followed by 7.56 g of anhydrous silver fluoride. The reaction mixture thus formed was then stirred at room temperature for 2 hours.

The reaction took place according to the following reaction scheme:

$$2CF_3SO_2Cl + ((CH_3)_3Si)_3N + 3AgF \rightarrow Ag(CF_3SO_2)_2N + 2AgCl + 3(CH_3)_3SiF\Delta$$

At the end of the reaction period the reaction mixture was filtered to separate off AgCl, insoluble in said mixture. The imide $Ag(CF_3SO_2)_2N$ was obtained as evaporation residue by evaporation of the filtrate to strip off the solvent. This imide is very soluble in aromatic solvents such as benzene and toluene.

EXAMPLE 12

2.67 g of pentafluorobenzenesulphonyl chloride were added to 10 ml of a 1M solution of potassium hexamethyldisilylamide in diglyme. A KCl precipitate formed.

The reaction took place according to the following reaction scheme:

$$C_6F_5SO_2Cl + K((CH_3)_3Si)_2N \rightarrow KCl + C_6F_5SO_2N(Si(CH_3)_3)_2$$

0.58 g of anhydrous KF and 3.02 g of perfluorobutanesulphonyl fluoride were added to the reaction mixture thus formed and the whole was stirred at room temperature for 3 hours.

A mixed imide was formed according to the following reaction scheme:

$$C_6F_5SO_2N(Si(CH_3)_3)_2 + KF + C_4F_9SO_2F \rightarrow K(C_6F_5SO_2NSO_2C_4F_9) + 2(CH_3)_3SiF \uparrow$$

At the end of the reaction period the reaction mixture was filtered to separate off the KCl, insoluble in the said mixture. The abovementioned mixed imide was isolated as distillation residue by distillation of the filtrate under reduced pressure to strip off the solvent.

EXAMPLE 13

4.4 ml of nonamethylsilazane were added to 20 ml of THF, maintained at −18° C., followed by 3.04 g of trifluoromethanesulphonyl fluoride. After returning to room temperature and stirring for 2 hours, 2.32 g of anhydrous KF and 4.37 g of pentafluoroethanesulphonyl chloride were then added to the reaction mixture and the whole was stirred at room temperature for 2 hours.

A mixed imide formed according to the following reaction scheme:

1) $CF_3SO_2F + ((CH_3)_3Si)_3N \rightarrow CF_3SO_2N(Si(CH_3)_3)_2 + (CH_3)_3SiF \uparrow$ 2) $CF_3SO_2N(Si(CH_3)_3)_2 + 2KF + C_2F_5SO_2Cl \rightarrow KCl + 2(CH_3)_3SiF \uparrow + K(CF_3SO_2NSO_2C_2F_5)$ At the end of the reaction period the reaction mixture was filtered to separate off KCl, insoluble in the said mixture. The filtrate was then evaporated down to strip off the solvent and the above mixed imide was obtained as the evaporation residue.

I claim:

1. A one-step method for synthesizing a sulphonylimide of the formula $$M((RSO_2)_2N)_y$$

wherein M is a metal or an ammonium radical $N(R_1)_4$, wherein the symbols $R_1$, which are identical or different, denote a hydrogen atom or a $C_1$-$C_8$ hydrocarbyl radical, R denotes a monovalent $C_1$-$C_{12}$ organic radical, and y is a number equal to the valency of M, said method comprising:

(A) reacting
  (i) a silazane compound of the formula $$M(((R_2)_3Si)_2N)_y$$

wherein $R_2$ is a $C_1$-$C_4$ alkyl and
  M and y have the above-mentioned meanings, and
  (ii) a sulphonyl fluoride of the formula $$RSO_2F$$

wherein R has the above-mentioned meaning in a molar ratio of said sulphonyl fluoride to said silizane compound substantially equal to 2y:1,; and
(b) recovering said sulphonylimide.

2. A method for synthesizing a sulphonylimide of the formula $$M_1((RSO_2)_2N)_z$$

wherein $M_1$ is a metal or an ammonium radical $N(R_1)_4$, wherein the symbols $R_1$, which are identical or different, denote a hydrogen atom or a $C_1$-$C_8$ hydrocarbyl radical, R denotes a monovalent $C_1$-$C_{12}$ organic radical, and z is a number equal to the valency of $M_1$, said method comprising:

(A) reacting
  (i) a silazane compound of the formula $$M(((R_2)_3Si)_2N)_y$$

wherein $R_2$ is a $C_1$-$C_4$ alkyl,
  M is a metal or an ammonium radical $N(R_1)_4$, wherein the symbols $R_1$, which are identical or different, denote a hydrogen atom or a $C_1$-$C_8$ hydrocarbyl radical, and
  y is a number equal to the valency of M,
  (ii) a fluoride of flow lattice energy of the formula $$M_1F_z$$

wherein $M_1$ and z have the above-mentioned meanings, and
  (iii) a sulphonyl chloride of the formula $$RSO_2Cl$$

wherein R has the above-mentioned meaning; and
(B) recovering said sulphonylimide.

3. A method for synthesizing a sulphonylimide of the formula $$M_1((RSO_2)_2N)_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R denotes a monovalent $C_1$–$C_{12}$ organic radical, and z is a number equal to the valency of $M_1$, said method comprising (A) reacting (i) a silazane compound of the formula $$AN(Si(R_2)_3)_2$$

wherein A denotes a hydrogen atom or an $(R_2)_3Si$ radical, and $R_2$ is a $C_1$–$C_4$ alkyl, (ii) a fluoride of low lattice energy of the formula $$M_1F_z$$

wherein $M_1$ and z have the above-mentioned meanings, and (iii) a sulphonyl chloride of the formula $$RSO_2F$$

or $$RSO_2Cl$$

wherein R has the above-mentioned meaning; and (B) recovering said sulphonylimide.

4. A method for synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R' are different and each denotes a monovalent $C_1$–$C_{12}$ organic radical, and z is a number equal to the valency of $M_1$, said method comprising:

(A) reacting (i) a silazane compound of the formula $$M_1(((R_2)_3Si)_2N)_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, $R_2$ is a $C_1$–$C_4$ alkyl, and z is a number equal to the valency of $M_1$, and (ii) a sulphonyl chloride of the formula $$RSO_2Cl$$

wherein

R denotes a monovalent $C_1$–$C_{12}$ organic radical, in a molar ratio of said sulphonyl chloride to said silazane compound substantially equal to z:1, to form a reaction mixture;

(B) reacting said reaction mixture with (i) a sulphonyl fluoride of the formula $$R'SO_2F$$

wherein R' denotes a monovalent $C_1$–$C_{12}$ organic radical which is different from R, and (ii) a fluoride of low lattice energy of the formula $$M_1F_z$$

wherein $M_1$ and z have the above-mentioned meanings, and wherein the molar ratio $R'SO_2F$:$RSO_2Cl$ is substantially equal to 1:1 and the molar ratio of $RSO_2Cl$:$M_1F_z$ is substantially at most z:1, and (C) recovering said sulphonylimide.

5. A method of synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R' are different and each denotes a monovalent $C_1$–$C_{12}$ organic radical, and z is a number equal to the valency of $M_1$, said method comprising:

(A) reacting (i) a silazane compound of the formula $$AN(Si(R_2)_3)_2$$

wherein A denotes a hydrogen atom or an $(R_2)_3Si$ radical, and $R_2$ is a $C_1$–$C_4$ alkyl, and (ii) a sulphonyl fluoride of the formula $$RSO_2F$$

wherein r denotes a monovalent $C_1$–$C_{12}$ organic radical, in a molar ratio of said sulphonyl fluoride to said silazane compound substantially equal to 1:1, to form a reaction mixture;

(B) reacting said reaction mixture with (i) a sulphonyl chloride of the formula $$R'SO_2Cl$$

wherein R' denotes a monovalent $C_1$–$C_{12}$ organic radical which is different from R, and (ii) a fluoride of low lattice energy of the formula $$M_1F_z$$

wherein $M_1$ and z have the above-mentioned meanings, and wherein, when A is $(R_2)_3Si$, the molar ratio of said sulphonyl chloride to said silazane compound is substantially equal to 1:1 and the molar ratio of $R'SO_2Cl$:$M_1F_z$ is at most substantially equal to z:2, and when A is a hydrogen atom, the molar ratio of said sulphonyl chloride to said silazane compound is substantially equal to 1:2 and the molar ratio $R'SO_2Cl$:$M_1F_z$ is at most substantially equal to z:2, and (C) recovering said sulphonylimide.

6. The method according to claims 1 or 2, wherein M denotes a metal of Groups I and II of the Periodic Table of the Elements, an $NH_4$ group or an $N(R_3)_4$ group wherein $R_3$ is a $C_1$–$C_6$ alkyl radical or a phenyl radical.

7. The method according to claim 4, wherein $M_1$ denotes a metal of Groups I and II of the Periodic Table of the Elements, an $NH_4$ group or an $N(R_3)_4$ group wherein $R_3$ is a $C_1$–$C_6$ alkyl radical or a phenyl radical.

8. The method according to any one of claims 1, 2, 3, 4 and 5, wherein R is a $C_1$–$C_{12}$ hydrocarbyl radical or a $C_1$–$C_{12}$ perfluorohydrocarbyl radical.

9. The method according to claim 8, wherein said $C_1$–$C_{12}$ perfluorohydrocarbyl radical is a $C_1$–$C_8$ perfluoroalkyl radical or a perfluorophenyl radical.

10. The method according to claims 4 or 5, wherein R′ is a $C_1$–$C_{12}$ hydrocarbyl radical or a $C_1$–$C_{12}$ perfluorohydrocarbyl radical.

11. The method according to claim 10, wherein said $C_1$–$C_{12}$ perfluorohydrocarbyl radical is a $C_1$–$C_8$ perfluoroalkyl radical or a perfluorophenyl radical.

12. The method according to any one of claims 1, 2, 3, 4 and 5, wherein $R_2$ is methyl or ethyl.

13. The method according to any one of claims 2, 3, 4 and 5, wherein $M_1F_z$ is KF, AgF or $N(R_4)_4F$, wherein the symbols $R_4$, which are identical or different, are hydrogen, $C_1$–$C_6$ alkyl or phenyl.

14. The method according to any one of claims 1, 2, 3, 4 and 5, wherein reaction is carried out in a solvent medium consisting of a polar aprotic solvent or a mixture of polar aprotic solvents.

15. The method according to claim 2, wherein the molar ratio of the sulphonyl chloride to the silazane compound is substantially equal to z:1.

16. The method according to claim 3, wherein the sulphonyl halide is $RSO_2F$, the molar ratio of the sulphonyl halide to the silazane compound is substantially equal to 2:1 when A is $(R_2)_3Si$ or to 3:2 when A is a hydrogen atom and the molar ratio of the silazane derivative to the fluoride $M_1F_z$ is at most substantially equal to z:1 when A is $(R_2)_3Si$ or 2z:1 when A denotes a hydrogen atom.

17. The method according to claim 3, wherein the sulphonyl halide is $RSO_2Cl$, the molar ratio of the sulphonyl halide to the silazane compound is substantially equal to 2:1 when A is $(R_2)_3Si$ or 3:2 when A is a hydrogen atom and the molar quantities c of the fluoride $M_1F_z$, a of the silazane compound and b of the sulphonyl halide are such that c is at least substantially equal to $$\frac{1}{z} \times (a + b)$$

when A is $(R_2)_3Si$ or to $$\frac{1}{z} \times \left(\frac{a}{2} + b\right)$$

when A is a hydrogen atom.

18. A method of synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R′ are different and each denotes a monovalent $C_1$–$C_{12}$ organic radical, and z is a number equal to the valency of $M_1$, said method comprising:

(A) reacting
(i) a silazane compound of the formula $$M[((R_2)_3Si)_2N]_y$$

wherein M is a metal or an ammonium radical $N(R_1)_4$, wherein the symbols $R_1$, which are identical or different, denote a hydrogen atom or a $C_1$–$C_8$ hydrocarbyl radical, $R_2$ is a $C_1$–$C_4$ alkyl, and y is a number equal to the valency of M, (ii) a sulphonyl chloride of the formula $$RSO_2Cl$$

wherein r denotes a monovalent $C_1$–$C_{12}$ organic radical, and (iii) a fluoride of low lattice energy of the formula $$M_1F_z$$

wherein $M_1$ and z have the above-mentioned meanings, and wherein the molar ratio of $RSO_2Cl$ to the silazane compound is substantially equal to y:1 and wherein the molar ratio of the compound $RSO_2Cl$ to the fluoride $M_1F_z$ is at most substantially equal to z:1, to form a reaction mixture;

(B) reacting said reaction mixture with a sulphonyl fluoride of the formula $R'SO_2F$ wherein R′ denotes a monovalent $C_1$–$C_{12}$ organic radical which is different from R and wherein the molar ratio $R'SO_2F:RSO_2Cl$ is substantially equal to 1:1, and (C) recovering said sulphonylimide.

19. A method of synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R′ are different and each denotes a monovalent $C_1$–$C_{12}$ organic radical, and z is a number equal to the valency of $M_1$, said method comprising:

(A) reacting
(i) a silazane compound of the formula $$M[((R_2)_3Si)_2N]_y$$

wherein M is a metal or an ammonium radical $N(R_1)_4$, wherein the symbols $R_1$, which are identical or different, denote a hydrogen atom or a $C_1$–$C_8$ hydrocarbyl radical, $R_2$ is a $C_1$–$C_4$ alkyl, and y is a number equal to the valency of M, and (ii) a sulphonyl fluoride of the formula $R'SO_2F$ wherein R′ denotes a monovalent $C_1$–$C_{12}$ organic radical and wherein the molar ratio of $R'SO_2F$ to the silazane compound is substantially equal to y:1, to form a reaction mixture;

(B) reacting said reaction mixture with
(i) a sulphonyl chloride of the formula $$RSO_2Cl$$

wherein R denotes a monovalent $C_1$–$C_{12}$ organic radical which is different from R′, and (ii) a fluoride of low lattice energy of the formula $$M_1F_z$$

wherein $M_1$ and z have the above-mentioned meanings and wherein the molar ratio of $RSO_2Cl$ to the fluoride $M_1F_z$ is at most substantially equal to z:1 and the molar ratio $R'SO_2F$:$RSO_2Cl$ is substantially equal to 1:1; and (C) recovering said sulphonylimide.

20. A method of synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R′ are different and each denotes a monovalent $C_1$–$C_{12}$ organic radical, and z is a number equal to the valency of $M_1$, said method comprising:

(A) reacting (i) a silazane compound of the formula $$M[((R_2)_3Si)_2N]_y$$

wherein M is a metal or an ammonium radical $N(R_1)_4$, wherein the symbols $R_1$, which are identical or different, denote a hydrogen atom or a $C_1$–$C_8$ hydrocarbyl radical, $R_2$ is a $C_1$–$C_4$ alkyl, and y is a number equal to the valency of M, (ii) a sulphonyl chloride of the formula $$RSO_2Cl$$

wherein $M_1$ and z have the above-mentioned meanings and wherein the molar ratio of $RSO_2Cl$ to the silazane compound is substantially equal to y:1 and wherein the molar ratio of the compound $RSO_2Cl$ to the fluoride $M_1F_z$ is at most substantially equal to z:1, to form a reaction mixture;

(B) reacting said reaction mixture with (i) a sulphonyl chloride of the formula $$R'SO_2Cl$$

wherein R′ denotes a monovalent $C_1$–$C_{12}$ organic radical which is different from R, and (ii) the fluoride of low lattice energy of the formula also used in step (A), wherein the molar ratio of $R'SO_2Cl$ to the fluoride $M_1F_z$ of step (B) is at most substantially equal to z:1 and the molar ratio $RSO_2Cl$:$R'SO_2Cl$ is substantially equal to 1:1; and (C) recovering said sulphonylimide.

21. A method of synthesizing a sulphonylimide of the formula $$M_1((RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R′ are different and each denotes a monovalent $C_1$–$C_{12}$ organic radical, and z is a number equal to the valency of $M_1$, said method comprising:

(A) reacting (i) a silazane compound of the formula $$AN(Si(R_2)_3)_2$$

wherein A denotes a hydrogen atom or an $(R_2)_3Si$ radical, and $R_2$ is a $C_1$–$C_4$ alkyl, (ii) a fluoride of fluoride of the low lattice energy of the formula $$M_1F_z$$

wherein $M_1$ and z have the above-mentioned meanings, and (iii) a sulphonyl fluoride of the formula $$RSO_2F$$

wherein R has the above-mentioned meaning and wherein the molar ratio of $RSO_2F$ to the silazane compound is substantially equal to 1:1 and the molar ratio of the silazine compound to the fluoride $M_1F_z$ is at most substantially equal to z:1 when A is $(R_2)_3Si$ or to 2z:1 when A denotes a hydrogen atom, to from a reaction mixture;

(B) reacting said reaction mixture with a sulphonyl fluoride of the formula $$R'SO_2F$$

wherein R′ denotes a monovalent $C_1$–$C_{12}$ organic radical which is different from R and wherein the molar ratio of $R'SO_2F$ to $RSO_2F$ is substantially equal to 1:1 when A is $(R_2)_3Si$ or to 1:0 when A denotes a hydrogen atom; and (C) recovering said sulphonylimide.

22. A method for synthesizing a sulphonylimide of the formula $$M_1(RSO_2NSO_2R')_z$$

wherein $M_1$ is a metal or an ammonium radical $N(R_1)_4$, wherein the symbols $R_1$, which are identical or different, denote a hydrogen atom or a $C_1$–$C_8$ hydrocarbyl radical, R and R′ are different and each denotes a monovalent $C_1$–$C_{12}$ organic radical, and z is a number equal to the valency of $M_1$, said method comprising:

(A) reacting (i) a silazane compound of the formula $$AN(Si(R_2)_3)_2$$

wherein

A denotes a hydrogen atom or an $(R_2)_3Si$ radical, and $R_2$ is a $C_1$–$C_4$ alkyl, (ii) a fluoride of the low lattice energy of the formula $$M_1F_z$$

wherein $M_1$ and $z$ have the above-mentioned meanings, and (iii) a sulphonyl halide of the formula $$RSO_2F \text{ or } RSO_2Cl$$

wherein
R has the above-mentioned meaning and wherein the molar ratio of $RSO_2F$:silazane compound or $RSO_2Cl$:silazane compound is substantially equal to 1:1, to form a reaction mixture;

(B) reacting said reaction mixture with a sulphonyl halide component selected from a sulphonyl fluoride $R'SO_2F$ or a mixture of a sulphonyl chloride $R'SO_2Cl$ and a fluoride $M_1F_z$ as also used in step (A), wherein $R'$ denotes a monovalent $C_1$-$C_{12}$ organic radical which is different from R and wherein the molar ratio of the sulphonyl halide of step (A) to the sulphonyl halide of step (B) is substantially equal to 1:1 when A is $(R_2)_3Si$ or 1:2 when A denotes a hydrogen atom; and (C) recovering said sulphonylimide.

* * * * *

UNITED STATES PATENT AND TRADEMARK OFFICE
CERTIFICATE OF CORRECTION

PATENT NO. : 5,256,821
DATED : OCTOBER 26, 1993
INVENTOR(S) : MICHEL B. ARMAND

It is certified that error appears in the above-indentified patent and that said Letters Patent is hereby corrected as shown below:

In the Abstract, line 4, "similar" should read --different--;

line 5, "hydrocarbyles" should read --hydrocarbyls--;

lines 5-6, "perfluorohydrocarbyles" should read --perfluorohydrocarbyls--;

line 9, "or" should read --and--;

line 11, "halogenite" should read --halogenide--;

line 15, "M" should read --$M_1$--.

Column 1, line 11, "sulthonylimides" should read --sulphonylimides--;

lines 17 and 18, "amides" should read --imides--;

line 20, "$CF_5$" should read --$C_6F_5$--;

line 36, "amides" should read --imides--.

UNITED STATES PATENT AND TRADEMARK OFFICE
CERTIFICATE OF CORRECTION

PATENT NO. : 5,256,821
DATED : OCTOBER 26, 1993
INVENTOR(S) : MICHEL B. ARMAND

It is certified that error appears in the above-indentified patent and that said Letters Patent is hereby corrected as shown below:

Column 2, lines 4 and 7, "amides" should read --imides--;

Column 3, line 26, "RSO$_2$CL" should read --RSO$_2$Cl--;

line 65, "MF" should read --M$_1$F$_z$--.

Column 4, line 21, "C$_1$-C$_2$" should read --C$_1$-C$_{12}$--;

line 25, "C$_1$-C$_6$" should read --C$_1$-C$_8$--;

line 26, "C$_5$F$_3$" should read --C$_6$F$_{13}$--.

Column 5, line 17, "M1" should read --M$_1$--;

line 59, "amides" should read --imides--.

Column 7, line 1, "C$_4$F$_9$SO$_2$F" should read --2C$_4$F$_9$SO$_2$F--;

line 9, "THP" should read --THF--;

line 40, "rithium" should read --lithium--.

Column 8, line 27, delete "sulphonyl" (second occurrence).

Column 10, line 22, "silizane" should read --silazane--;

line 49, "flow" should read --low--.

Column 11, line 19, "chloride" should read --halide--.

UNITED STATES PATENT AND TRADEMARK OFFICE
CERTIFICATE OF CORRECTION

PATENT NO. : 5,256,821
DATED : OCTOBER 26, 1993
INVENTOR(S) : MICHEL B. ARMAND

It is certified that error appears in the above-indentified patent and that said Letters Patent is hereby corrected as shown below:

Column 12, line 36, "r" should read --R--.

Column 14, line 16, "r" should read --R--.

Column 15, line 39, after "$RSO_2Cl$", beginning on a new line, insert --wherein R denotes a monovalent $C_1$-$C_{12}$ organic radical, and (iii) a fluoride of low lattice energy of the formula $M_1F_z$--.

Column 16, line 14, delete "fluoride of the";

line 31, "form" should read --from--;

line 41, "1:0" should read --1:2--.

Signed and Sealed this

Twenty-third Day of August, 1994

BRUCE LEHMAN

Attest:

Attesting Officer

Commissioner of Patents and Trademarks